United States Patent [19]

Offermanns et al.

[11] Patent Number: 6,028,244

[45] Date of Patent: Feb. 22, 2000

[54] DEFECTIVE PLATELET ACTIVATION IN $G\alpha_Q$ DEFICIENT MICE

[75] Inventors: Stefan Offermanns, Johannisberger, Germany; Christopher F. Toombs, Camarillo, Calif.

[73] Assignee: California Institute of Technology, Pasadena, Calif.

[21] Appl. No.: 09/096,366

[22] Filed: Jun. 11, 1998

Related U.S. Application Data

[60] Provisional application No. 60/049,753, Jun. 11, 1997.

[51] Int. Cl.$^7$ .............................. C07H 21/04; C12N 5/00; C12N 5/06; C12N 5/10; C12N 15/00
[52] U.S. Cl. ...................... 800/18; 435/320.1; 435/325; 435/354; 435/455; 435/463; 536/23.1; 536/23.5; 800/21; 800/23; 800/25
[58] Field of Search .................................. 800/3, 8, 9, 13, 800/14, 15, 16, 17, 18, 19, 20, 21, 23, 25; 514/44; 536/23.1, 23.5

[56] References Cited

PUBLICATIONS

Hepler, J.R., and Gilman, A.G., 1992, "G Proteins," Trends Biochem Sci 17:383–387.

Laugwitz, K.L., et al., 1996 Jan, "The human thyrotropin receptor: a heptahelical receptor capable of stimulating members of all four G protein families," Proc Natl. Acad Sci USA, 93(1): 116–120.

McClintock, T.S., et al., 1997 Jun., "Molecular cloning of a lobster G alpha(q) protein expressed in neurons of olfactory organ and brain," J. Neurochem 68:2248–2254.

Neer, E.J., 1995, "Heterotrimeric G Proteins: Organizers of Transmembrane Signals," Cell 80:246–257.

Offermanns, S., et al., 1994 Jan, "G proteins of the G12 family are activated via thromboxane A2 and thrombin receptors in human platelets, "Proc Natl Acad Sci USA, 91(1):504–508.

Offermanns, S., and Simon, M.I., 1995 Jun, "G alpha 15 and G alpha 16 Couple a Wide Variety of Receptors to Phospholipase C," J Biol Chem, 170(25):15175–15180.

Offermanns, S., et al., 1997 Sep, "Defective platelet activation in G$\alpha_g$–deficient mice," Nature, 389:183–186.

Offermanns, S., et al., 1997 Dec, "Impaired motor coordination adn persistent multiple climbing fiber innervation of cerebellar Purkinje cells in mice lacking G $\alpha$," Proc Natl Acad Sci 94(25);14089–94.

Shenker, A., et al., 1991, "The G Protein Coupled to the Thromboxane A2 Receptor in Human Platelets Is a Member of the Novel Gq Family," J. Biol. Chem 266(14):9309–9313.

Offermanns, S., and Schultz, G., 1994 Oct, "Complex information processing by the transmembrane signaling system involving G proteins, "Naunyn Schmiedebergs Arch Pharmacol, 350(1):329–338.

Wall, RJ Transgenic livestock: Progress and prospects for the future. Theriogenology 45: 57–68, 1996.

Mullins et al. Fulminant hypertension in transgenic rats harboring the mouse Ren–2 gene. Nature 344: Apr. 1990.

Hammer et al. Spontaneous inflammatory disease in transgenic rats expressing HLA–B27 and human b2m: An animal model of HLA–B27 associated disorders. Cell 63: 1099–1112, Nov. 1990.

Mullins et al. Expression of the DBA/2J Ren–2 gene in teh adrenal gland of transgenic mice. EMBO J. 8:4065–4072, 1989.

Taurog et al. HLA–B27 in inbred and non–inbred transgenic mice. J. Immunol. 141: 4020–4023, Dec. 1988.

Evans and Kaufman Establishment in culture of pluripotenial cells from mouse embryos. Nature 292:154–156, Jul. 1981.

Strathmann et al. G protein diversity: A distinct class of alpha subunits is present in vertebrates and invertebrates. PNAS 87:9113–9117, Dec. 1990.

DeChiara et al. A growth–deficiency phenotype in heterozgous mice carrying an insulin–like growth factor II gene disrupted by targeting. Nature 345:78–80, May 1990.

Gordon et al. Genetic transformation of mouse embryos by microinjection of purified DNA. PNAS 77:7380–7384, Dec. 1980.

Huszar et al. Insertion of bacterial gene into the mouse germ line using an infectious retrovirus vector. PNAS 82:8587–8591, Dec. 1985.

Bradley et al. Modifying the mouse: Design and desire. Bio/Technology 10: 534–539, May 1992.

Campbell and Wilmut Totipotency or multipotentiality of cultured cells: Applications and progress. Theriogenology 47:63–72, Jan. 1997.

D'Angelo et al. Transgenic Galphaq overexpression induces cardiac contractile failure in mice. PNAS 94:8121–8126, Jul. 1997.

Schlager et al. Spontaneous mutations and mutation rates in the house mouse. Genetics 57:319–330, Oct. 1967.

Orkin, SH and Motulsky, AG Report and recommendations of the panel to assess to NIH investment in research on gene therapy, Dec. 1995.

Friedmann, T Overcoming the obstacles to gene therapy. Sci. Am. Jun. 1997 pp. 96–101, Jun. 1997.

Verma et al. Gene therapy—promises, problems and prospects. Nature 389:239–242, Sep. 1997.

*Primary Examiner*—Bruce R. Campell
*Assistant Examiner*—Anne-Marie Baker
*Attorney, Agent, or Firm*—Fish & Richardson P.C.

[57] ABSTRACT

The invention provides a nonhuman transgenic animal having a transgene disrupting or interfering with expression of $G\alpha_q$ chromosomally integrated into the germ cells of the animal. Cells and cell lines derived from these nonhuman transgenic animals; a method for producing a transgenic nonhuman animal having a phenotype characterized by expression of a transgene which is otherwise not naturally occurring, where the expression of the transgene disrupts or interferes with $G\alpha_q$ activity; a method for determining an effect of an agent on $G\alpha_q$ expression, by administering an effective amount of the agent to a transgenic nonhuman animal having a transgene disrupting or interfering with $G\alpha_q$, and measuring a physiological response of the transgenic nonhuman animal to the agent, and comparing the physiological response of the transgenic nonhuman animal having a transgene disrupting or interfering with $G\alpha_q$ to a control animal is also provided.

10 Claims, 2 Drawing Sheets

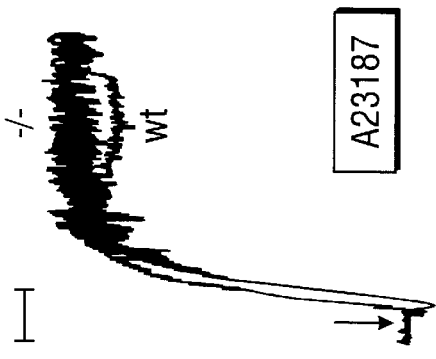
FIG. 1A ADP
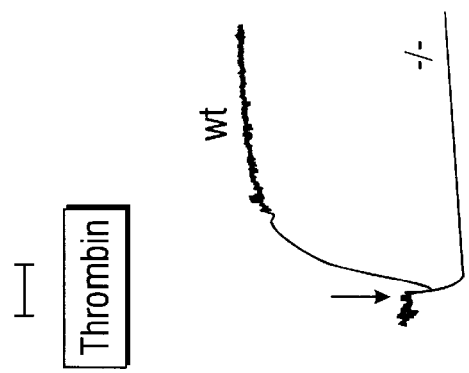
FIG. 1B Thrombin
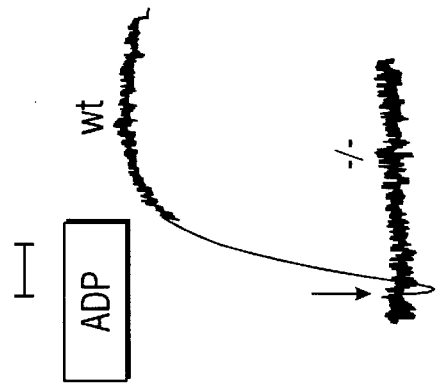
FIG. 1C Collagen
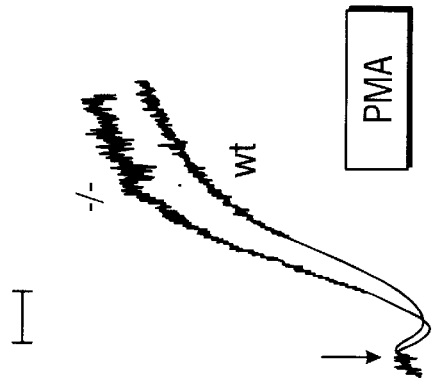
FIG. 1E A23187
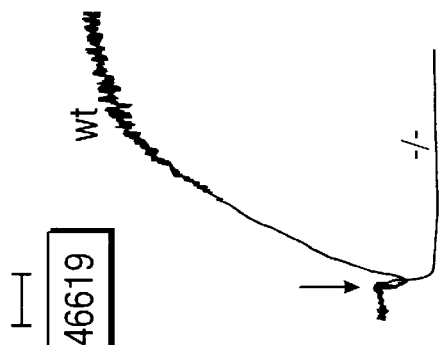
FIG. 1D U46619
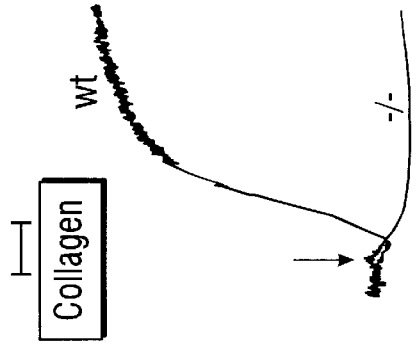
FIG. 1F PMA

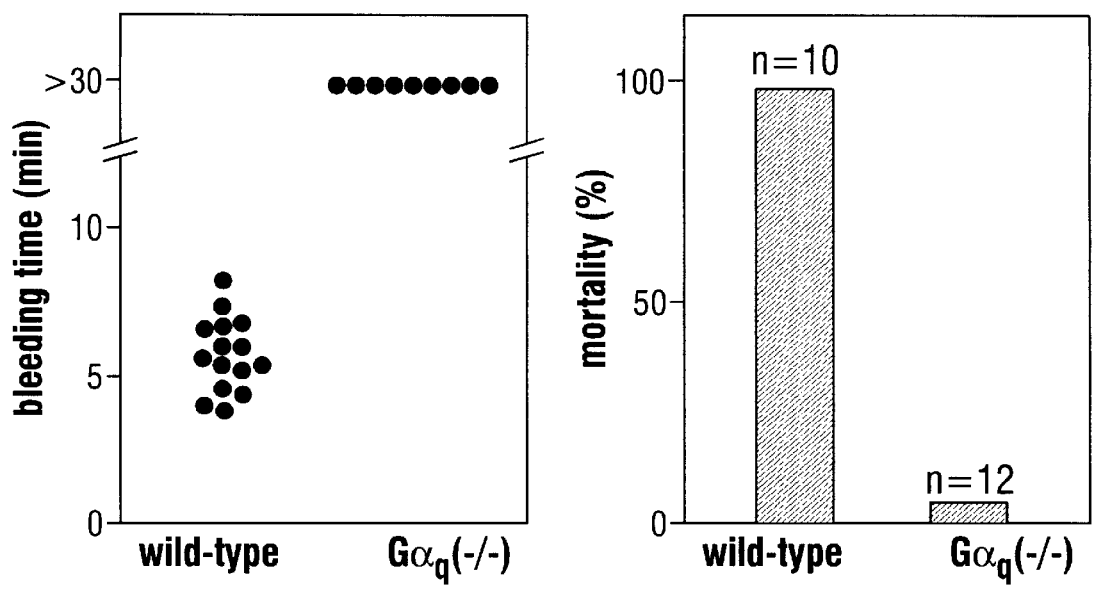
FIG. 2A  FIG. 2B
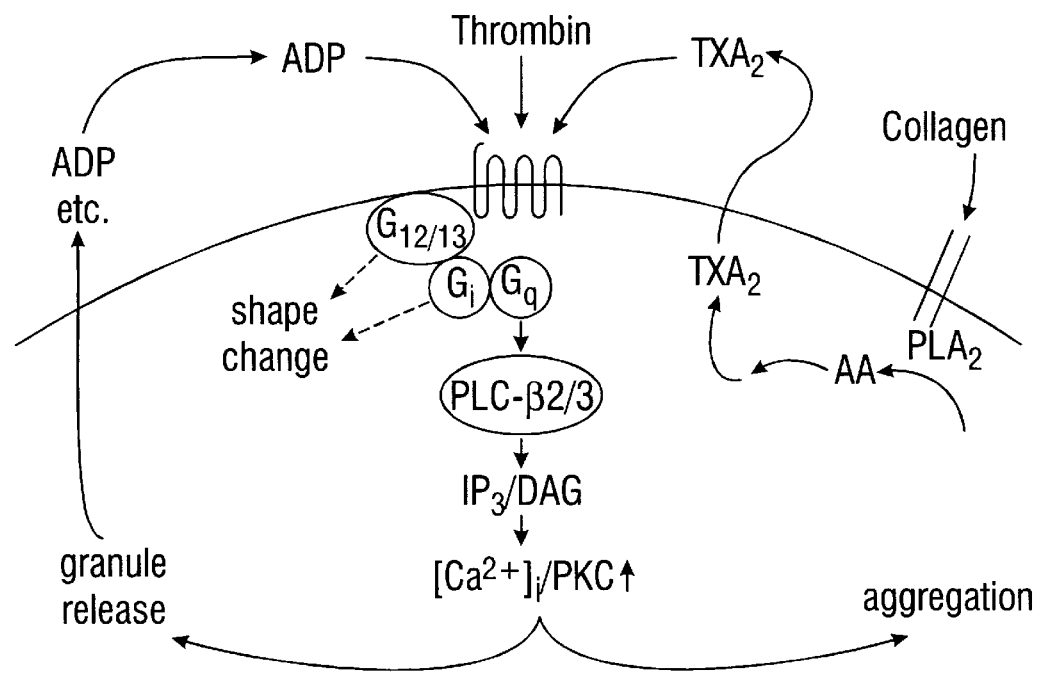
FIG. 2C

6,028,244

DEFECTIVE PLATELET ACTIVATION IN $G\alpha_Q$ DEFICIENT MICE

CROSS REFERENCE TO RELATED APPLICATIONS

This application claims priority under 35 USC §119 (e)(1) from provisional application Ser. No. 60/049,753, filed Jun. 11, 1997.

FIELD OF THE INVENTION

This invention relates to platelet activation and more specifically to the role of $G\alpha_q$ in platelet activation and the design of therapeutic agents targeted to $G\alpha_q$.

BACKGROUND OF THE INVENTION

A G protein is a heterotrimeric guanine nucleotide binding regulatory protein, generally localized to the inner surface of the plasma membrane where it transduces signals from transmembrane receptors to intracellular effectors. In the resting state, the G protein exists as a trimer containing α, β, and γ subunits. Interaction of the G protein with agonist-bound receptor stimulates the exchange of GTP for GDP on the a subunit, and the α and γ subunit dissociate from the activated a subunit. The GTP-bound α subunit and the free β/γ complex can act independently on downstream effectors to modulate second messenger concentrations. The hydrolysis of GTP to GDP deactivates the a subunit, thereby allowing the reassociation of the α and β/γ complex the recoupling of the heterotrimer to the receptor (Casey, P. J., *Curr. Opin. Cell Biol.* 6: 219–225, 1994).

Platelets are small disc-shaped cell fragments which undergo a rapid transformation when they encounter sites of vascular damage. They become more spherical and extrude pseudopodia, their fibrinogen receptors are activated leading to aggregation, and they release their granule contents and eventually they form a plug which is responsible for primary hemostasis (Siess, W., *Physiol. Rev.* 69: 58–178, 1989). Activation of platelets is also implicated in the pathogenesis of unstable angina, myocardial infarction and stroke (Packham, M. A., *Can J. Physiol Pharmacol.* 72: 278–284).

Several physiological substances are involved in the activation of platelets such as collagen, which is exposed at the subendothelial surfaces, thrombin, generated by the coagulation cascade, and thromboxane $A_2$ ($TXA_2$) and ADP, which are released from activated platelets. Collagen binds to several platelet membrane proteins including integrin $\alpha_2\beta_1$ leading to platelet activation through the release of $TXA_2$ and ADP (Shattil, S. J., et al., *Curr. Opin. Cell Biol.* 6: 695–704, 1994). In contrast, thrombin, $TXA_2$, and ADP, activate G-protein coupled receptors directly and induce platelet aggregation and granule release (Hourani, S. M, and Cusack, N. J., *Pharmacol. Rev.* 43: 243–298, 1991). The receptors for these platelet activators have been shown to couple to several G-proteins, including $G_i$, $G_q$, $G_{12}$, and $G_{13}$ (see, for example, Shenker, A., et al., *J. Biol. Chem.* 266: 9309–9313, 1991). These G-proteins have been shown to regulate different effectors (Neer, E. I., *Cell* 80: 246–257, 1995; Hepler, J. R., and Gilman, A. G., *Trends Biochem. Sci.* 17: 383–387, 1992).

The major events involved in platelet activation are believed to be the result of the activation of β-isoforms of phospholipase C (PLC) leading to the generation of inositol 1,4,5 triphosphate and diacylglycerol. It is not clear whether G-protein mediated release of "β"γ-subunits or the activation of $G_q$ is the predominant mechanism for PLC-β activation in platelets. Platelets mainly contain two isoforms, PLC-β2 and PLC-β3 (Lee, S. B., et al., *Blood* 88: 1684–1691, 1996; Bonno, Y., et al., *J. Biol. Chem.* 271: 14989–14994, 1996). While PLC-β2 is only weakly activated by $G\alpha_{q/11}$ when compared with PLC-β3, both enzymes appear to be regulated by G-protein βγ-subunits. Most mammalian tissues express $G\alpha_q$ together with its close structural and functional homolog $G\alpha_{11}$. Platelets are, however, an exception.

SUMMARY OF THE INVENTION

This invention is based on the finding that $G\alpha_q$ plays a key role in platelet activation. The invention provides a nonhuman transgenic animal having a transgene disrupting or interfering with expression of $G\alpha_q$ chromosomally integrated into the germ cells of the animal. Cells and cell lines derived from these nonhuman transgenic animals are also provided.

In one embodiment, transgenic non-human animals and a method for producing a transgenic nonhuman animal having a phenotype characterized by expression of a transgene which is otherwise not naturally occurring, where the expression of the transgene disrupts or interferes (e.g., decreases or inhibits) with $G\alpha_q$ expression or activity are provided. The method includes introducing a transgene in operable linkage with at least one expression regulatory sequence into a zygote of an animal; transplanting the zygote of the first step into a pseudopregnant animal; allowing the zygote to develop to term, and identifying at least one transgenic offspring, where expression of the transgene disrupts or interferes with $G\alpha_q$ expression or activity. Also included are progeny, cells, tissues, and the like from such transgenic animals.

In another embodiment, a method is provided for determining an effect of an agent on $G\alpha_q$ expression. The method includes administering an effective amount of the agent to a transgenic nonhuman animal having a transgene disrupting or interfering with $G\alpha_q$, and measuring a physiological response of the transgenic nonhuman animal to the agent, and comparing the physiological response of the transgenic nonhuman animal having a transgene disrupting or interfering with $G\alpha_q$ to a control animal, wherein the same physiological response in the transgenic nonhuman animal as compared to the control animal indicates the specificity of the agent.

The invention further provides a method of determining an adverse drug interaction with a $G\alpha_q$-inhibitor. This method includes administering a test amount of an agent to a transgenic nonhuman animal having a transgene disrupting or interfering with $G\alpha_q$, and comparing a physiological reaction of the transgenic animal to a physiological reaction of a nontransgenic animal of the same species administered the test amount of the agent. An adverse response in the transgenic animal as compared to the nontransgenic animal is indicative of an adverse drug interaction with a $G\alpha_q$-inhibitor.

In yet another embodiment, a method is provided of treating a $G\alpha_q$-related disorder, including administering to a subject a therapeutically effective amount of an agent which affects $G\alpha_q$ expression or function in platelets.

BRIEF DESCRIPTION OF THE DRAWINGS

FIG. 1 is a series of graphs showing the aggregation response of wild-type (wt) and $G\alpha_q$ deficient (−/−) platelet rich plasma. In each panel, the addition of stimuli is signified by the arrow, and the horizontal bar at the upper left is a time reference indicating one minute. The graphs show that platelets from $G\alpha_q$ (−/−) mice did not aggregate in response to 10 μM ADP (Panel a), 1 U/ml thrombin (Panel b), 10 μg/ml collagen (Panel c) and 10 μg/ml of the thromboxane $A_2$ mimetic, U46619 (Panel d). $G\alpha_q$ deficient platelets, however, responded with pronounced shape change to thrombin, collagen and U46619. In contrast, the aggregation response to all four agonists was present in platelets from wild-type littermates. Wild-type platelets and $G\alpha_q$ deficient platelets were equally responsive to 100 μM calcium ionophore A23187 (Panel e) and to 100 μM phorbol ester phorbol 1 2-myristate 13-acetate (Panel f).

FIG. 2 illustrates various assays of hemostasis and thromboembolism. Panel a is a plot of tail bleeding times (min) for 15 wild-type and 9 $G\alpha_q$ (−/−) littermates. Panel b is a bar graph illustrating the protection of $G\alpha_q$ (−/−) mice from thrombotic challenge. Shown is the percentage of wild-type (n=10) and $G\alpha_q$ deficient mice (n=12) which died following fatal thromboembolism induced by intravenous collagen/epinephrine injection. One out of 12 tested $G\alpha_q$ (−/−) mice died 10 min after injection of collagen/epinephrine due to massive bleeding from the site of injection. Panel c shows a simplified model emphasizing the role of $G_q$ in the initiation of platelet activation.

DESCRIPTION OF THE PREFERRED EMBODIMENTS

Based on the finding that $G\alpha_q$ plays a role in platelet activation, provided herein are nonhuman transgenic animals and methods of making, methods for screening for compounds that affect $G\alpha_q$, and methods of treating $G\alpha_q$-related disorders, such as thrombotic-related disorders (e.g., stroke).

Transgenic Animals and Methods of Making the Same

In one embodiment, the present invention provides nonhuman transgenic animals having a disruption of a $G\alpha_q$ gene such that expression and/or biological activity ("activity") of $G\alpha_q$ is affected. For example, the disruption decreases or inhibits $G\alpha_q$ gene expression and/or biological activity. The term "animal" as used herein denotes all species except human. It also includes an individual animal in all stages of development, including embryonic and fetal stages. Farm animals (e.g., bovine, porcine, ovine and avian animals (cow, pig, sheep and birds), and other animals such as horses, rabbits and the like, rodents (such as mice), and domestic pets (e.g., cats and dogs) are included within the scope of the present invention. In a preferred embodiment the animal is a mouse or a rat.

A "transgenic" animal is any animal containing cells that bear genetic information received, directly or indirectly, by deliberate genetic manipulation at the subcellular level, such as by microinjection or infection with recombinant virus. These genetic manipulation results in the inclusion of exogenous genetic material in cells of the animal. By "exogenous" is meant genetic material that is not immediately contiguous with both of the coding sequences with which it is immediately contiguous (one on the 5' end and one on the 3' end) in the naturally occurring genome of the organism from which it is derived. "Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the present invention also contemplates the use of extrachromosomally replicating DNA sequences, such as might be engineered into yeast artificial chromosomes.

The term "transgenic animal" also includes a "germ cell line" transgenic animal. A germ cell line transgenic animal is a transgenic animal in which the genetic information has been taken up and incorporated into a germ line cell, therefore conferring the ability to transfer the information to offspring. If such offspring in fact possess some or all of that information, then they, too, are transgenic animals. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene chromosomally integrated therein.

When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a recently published procedure by Love et al., (*Biotechnology*, 12(1): 60–63, 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity.

When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

Embryonal target cells at various developmental stages can be used to introduce transgenes. Different methods are used depending on the stage of development of the embryonal target cell. The zygote is the best target for microinjection. The use of zygotes as a target for gene transfer has a major advantage in that in most cases the injected DNA will be incorporated into the host gene before the first cleavage (Brinster et al., *Proc. Natl. Acad. Sci. USA* 82: 4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

In the microinjection method useful in the practice of the subject invention, the transgene is digested and purified free from any vector DNA, e.g., by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, Penolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken β-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retroviral infection (Jaenich, R., *Proc. Natl. Acad. Sci USA* 73: 1260–1264, 1976). Efficient infection of the blastomeres is obtained by enzymatic treatment to remove the zona pellucida (Hogan et al. in *Manipulating the Mouse Embryo*, Cold Spring Harbor Laboratory Press, Cold Spring Harbor, N.Y., 1986). The viral vector system used to introduce the transgene is typically a replication-defective retrovirus carrying the transgene (Jahner, et al., *Proc. Natl. Acad. Sci. USA* 82: 6927–6931, 1985; Van der Putten, et al., *Proc. Natl. Acad. Sci USA* 82: 6148–6152, 1985). Transfection is easily and efficiently obtained by culturing the blastomeres on a monolayer of virus-producing cells (Van der Putten, supra; Stewart, et al., *EMBO J.* 6: 383–388, 1987). Alternatively, infection can be performed at a later stage. Virus or virus-producing cells can be injected into the blastocoele (D. Jahner et al., *Nature* 2-98: 623–628, 1982). Most of the founders will be mosaic for the transgene since incorporation occurs only in a subset of the cells which formed the transgenic nonhuman animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (Evans, M. J., et al., *Nature* 292: 154–156, 1981; Bradley, M. O., et al., *Nature* 309: 255–258, 1984; Gossler, et al., *Proc. Natl. Acad Sci USA* 83: 9065–9069, 1986; and Robertson et al., *Nature* 322:445–448, 1986). Transgenes can be efficiently introduced into the ES cells by DNA transfection or by retrovirus-mediated transduction. Such transformed ES cells can thereafter be combined with blastocysts from a nonhuman animal. The ES cells thereafter colonize the embryo and contribute to the germ line of the resulting chimeric animal. (For review, see Jaenisch, R., *Science* 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

A "transgene" is any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode $G\alpha_q$ antisense and $G\alpha_q$ dominant negative polypeptides, which may be expressed in a transgenic non-human animal. The transgenes of the invention also include DNA sequences which can, by homologous recombination or other methods, result in the disruption of an endogenous $G\alpha_q$ gene. In a specific aspect of the invention, the genomic clone used for gene targeting contained the two last exons of the $G\alpha_q$ gene. To generate a null mutation, a 2.3-kb Bg/II fragment containing an exon coding for amino acids 246–297 of $G\alpha_q$ was replaced by the neo gene from plasmid pMC1 neo PolyA (Stratagene). The targeting vector contained 5.5 kb of upstream sequence as the 5' arm and 2.6 kb of intron sequence as the 3' arm. Such a transgene construct is included in the invention. Other heterlogous nucleic acid sequences, such as neo described herein can be utilized to create a mutation.

The term "transgenic" as used herein additionally includes any organism whose genome has been altered by in vitro manipulation of the early embryo or fertilized egg or by any transgenic technology to induce a specific gene knockout. The term "gene knockout" as used herein refers to the targeted disruption of a gene in vivo with complete loss of function that has been achieved by any transgenic technology familiar to those in the art (e.g., see U.S. Pat. Nos. 5,589,369 issued Dec, 31, 1996, 5,612,205 issued Mar. 18, 1997 and 5,627,059 issued May 6, 1997 herein incorporated herein by reference). In one embodiment, transgenic animals having gene knockouts are those in which the target gene has been rendered nonfunctional by an insertion targeted to the gene to be rendered nonfunctional by homologous recombination. As used herein, the term "transgenic" includes any transgenic technology familiar to those in the art which can produce an organism carrying an introduced transgene or one in which an endogenous gene has been rendered nonfunctional or "knocked out." An example of a transgene used to "knockout" $G\alpha_q$ function is described in the Examples section.

The transgene to be used in the practice of the subject invention is a DNA sequence comprising a modified $G\alpha_q$ coding sequence (Offermanns, S., et al., *Proc. Natl. Acad Sci. USA* 94: 14089–14094, 1997; Offermanns, S., et al., *Nature* 389: 183–186, 1997, both herein incorporated by reference). In a preferred embodiment, the $G\alpha_q$ gene is disrupted by homologous targeting in embryonic stem cells. For example, the entire mature C-terminal region of the $G\alpha_q$ gene may be deleted. Optionally, the $G\alpha_q$ disruption or deletion may be accompanied by insertion of or replacement with other DNA sequences, such as a nonfunctional $G\alpha_q$ sequence. In other embodiments, the transgene comprises DNA antisense to the coding sequence for $G\alpha_q$ or comprises a ribozyme targeted to $G\alpha_q$ mRNA. In yet another embodiment, the transgene comprises DNA encoding an antibody or receptor peptide sequence which is able to bind to $G\alpha_q$. The DNA and peptide sequences of $G\alpha_q$ are known in the art, the sequences, localization and activity disclosed in McClintock, T. S., et al., *J. Neurochem.* 68: 2248–2254, 1997, herein incorporated by reference. Where appropriate, DNA sequences that encode proteins having altered $G\alpha_q$ activity, but differ in nucleic acid sequence, such as a dominant negative mutation, may be utilized. In addition sequences which differ due to the degeneracy of the genetic code may also be used herein as may truas may truncated forms of the $G\alpha_q$ sequences.

The invention also includes animals having heterozygous mutations in $G\alpha_q$ or partial inhibition of $G\alpha_q$ function or expression. A heterozygote would exhibit an intermediate level of platelet activation as compared to the homozygote. In other words, partial loss of function leads to a partial loss of the ability of platelets to aggregate. One of skill in the art would readily be able to determine if a particular mutation or if an antisense molecule was able to partially inhibit $G\alpha_q$. For example, in vitro testing may be for the presence of $G\alpha_q$ protein (e.g., Western blotting), or for the ability of platelets to aggregate and release ATP in response to collagen, arachidonic acid, thrombin, and the $TXA_2$ receptor antagonist U46616 (see examples below), or may be a bioassay for blood clotting.

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood samples using transgene specific probes. PCR is particularly useful in this regard. Positive progeny (GO) are crossbred to produce offspring (G1) which are analyzed for transgene expression by Northern blot analysis of tissue samples. To be able to distinguish expression of a transgene, such as an dominant-negative $G\alpha_q$ gene, from expression of the animals endogenous $G\alpha_q$ gene(s), a marker gene fragment can be included in the construct in the 3' untranslated region of the transgene and the Northern probe designed to assess the presence of the marker gene fragment.

The level of $G\alpha_q$ expressed on platelets can also be measured in the transgenic animal to establish appropriate expression. Expression of the $G\alpha_q$ transgenes can decrease the $G\alpha_q$ in the tissue and blood of the transgenic animals and consequently decrease the aggregation of platelets in response to agents such as collagen, arachidonic acid, thrombin and U46619. By practice of the subject invention, a statistically significant decrease in the aggregation of platelets in response to agents such as collagen, arachidonic acid, thrombin and U46619 can be obtained. Alternatively, alterations in a coagulation test, such as prolonged activated partial thromboplastin time (aPTT), prolonged prothombin time (PT), or prolonged thrombin time (TT) can be measured.

Transgenic mice can be produced carrying nucleic acid sequences that interfere with $G\alpha_q$ expression at the translational level. This approach utilizes, for example, antisense nucleic acid and ribozymes to block translation of a specific $G\alpha_q$ mRNA, either by masking that mRNA with an antisense nucleic acid or by cleaving it with a ribozyme. In addition, dominant-negative $G\alpha_q$ mutants can be used to actively interfere with function of "normal" $G\alpha_q$.

Antisense nucleic acids are DNA or RNA molecules that are complementary to at least a portion of a specific mRNA molecule (Weintraub, *Scientific American,* 262: 40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded.

Antisense oligomers of about 15 nucleotides are preferred, since they are easily synthesized and are less likely to cause problems than larger molecules when introduced into the target $G\alpha_q$-producing cell. The use of antisense methods to inhibit the in vitro translation of genes is well known in the art (Marcus-Sakura, *Anal Biochem.,* 172: 289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.,* 260: 3030, 1988). A major advantage of this approach is that, because they are sequence-specific, only mRNAs with particular sequences are inactivated.

There are two basic types of ribozymes namely, tetrahymena-type (Hasselhoff, *Nature,* 334: 585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

In another embodiment of the present invention, a nucleotide sequence encoding a $G\alpha_q$ dominant negative protein is provided. For example, a genetic construct that contains such a dominant negative encoding gene may be operably linked to a promoter, such as a tissue-specific promoter. For example, a megacaryocyte specific promoter (e.g., c-mpl) e.g., PF4 promoter (PNAS 88, 1521–1525, 1991)) or developmentally specific promoter (e.g., MCL2v promoter (Development 1251, 1943–1949, 1998)), or an inducible promoter (e.g., Doxycycline-dependent promoter (PNAS 93, 10933–38, 1998)) can be used in the subject invention.

$G\alpha_q$ most likely forms heterodimers with other guanine nucleotide binding protein family members, such as $G\alpha_{11}$. Hence, while not wanting to be bound by a particular theory, the dominant negative effect described herein may involve the formation of nonfunctional heterodimers of dominant negative $G\alpha_q$ monomers with other guanine nucleotide binding protein family members. More specifically, it is possible that any nonfunctional heterodimers formed by the dimerization of wild-type and/or dominant negative $G\alpha_q$ monomers produces a dominant effect by: 1) being synthesized but not processed or secreted; 2) inhibiting the secretion of wild type $G\alpha_q$; 3) preventing normal processing of the protein thereby producing a nonfunctional $G\alpha_q$ molecule; 4) altering the affinity of the nonfunctional dimer to a receptor or generating an antagonistic form of $G\alpha_q$ that binds a receptor without activating it; or 5) inhibiting the intracellular processing or secretion of $G\alpha_q$ or related proteins.

Nonfunctional $G\alpha_q$ that can function to inhibit platelet activation that includes a dominant negative $G\alpha_q$. Deletion or missense dominant negative forms of $G\alpha_q$ that retain the ability to form heterodimers but do not function as wild-type $G\alpha_q$ proteins may be used to inhibit the biological activity of endogenous wild-type $G\alpha_q$. Alternatively, a nonfunctional $G\alpha_q$ can function as a monomeric species to inhibit the platelet regulating actions of $G\alpha_q$.

Any genetic recombinant method in the art may be used to express an antisense nucleic acid directed against $G\alpha_q$ mRNA or a dominant negative $G\alpha_q$. For example, recombinant viruses may be engineered to express a dominant negative form of $G\alpha_q$ which may be used to inhibit the activity of wild-type $G\alpha_q$. Such viruses may also be used therapeutically for treatment of diseases resulting from aberrant over-expression or activity of $G\alpha_q$ protein, such as in clotting disorders.

Use of Transgenic Mice

In a method of the invention, a transgenic nonhuman animal can be used to analyze an effect of an agent on $G\alpha_q$ activity or expression. For example, an effective amount of an agent can be administered to the transgenic animal, and a physiological response of the animal to the agent is measured. The response of the treated transgenic animal is then compared to that of an untreated control animal.

A "physiological response" is any biological or physical parameter of an animal which can be measured. Molecular assays (e.g., gene transcription, protein production and degradation rates), physical parameters (e.g., exercise physiology tests, measurement of various parameters of respiration, measurement of heart rate or blood pressure, measurement of bleeding time, aPTT.T, or TT), and cellular assays (e.g,. immunohistochemical assays of cell surface markers, or the ability of cells to aggregate or proliferate) can be used to assess a physiological response. One example of a measurement of physiological response is a measurement of platelet activation. Platelet activation can be measured by several assays, including, but not limited to, measurements of platelet aggregation in response to agents such as ADP thrombin, A23187, collagen, U46619, or PMA, or measurement of bleeding time, or measurement of $Ca^{2+}$ mobilization in platelets in the presence of agents such as thrombin, U46619, or ADP. Alternatively, alterations in coagulation can be measured using standard assays well known to one of skill in the art such as activated partial thromboplastin time (aPTT), prothombin time (PT), or thrombin time (TT).

The agent to be tested for its effect on $G\alpha_q$ activity or expression can be a $G\alpha_q$-inhibitory agent. Of particular interest are agents that have a low toxicity for human cells. The term "$G\alpha_q$-inhibitory agent" as used herein describes any molecule, e.g., a protein, peptide, or pharmaceutical, with the capability of altering or mimicking the physiological function of $G\alpha_q$. A plurality of agents can be tested in parallel, and a variety of different concentrations of an agent can also be tested in order to assess a differential response to the various concentrations. Typically, one of these concentrations can serve as a negative control, i.e., zero concentration can serve as the control.

Candidate agents encompass numerous chemical classes, though typically they are organic molecules, preferably small organic agents having a molecular weight of more than 50 and less than about 2,500 Daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural agents. For example, numerous means are available for random and directed synthesis of a wide variety of organic agents and biomolecules, including expression of randomized oligonucleotides and oligopeptides. Alternatively, libraries of natural agents in the form of bacterial, fungal, plant and animal extracts are available or readily produced. Additionally, natural or synthetically produced libraries and agents are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In order to determine if an agent can affect $G\alpha_q$ expression, an effective amount of the agent can be administered to a transgenic animal having a transgene disrupting or interfering with $G\alpha_q$ expression or activity, and a physiological response of the transgenic animal can be measured, as described above. The method includes administering an effective amount of the agent to a transgenic nonhuman animal having a transgene disrupting or interfering with $G\alpha_q$, and measuring a physiological response of the transgenic nonhuman animal to the agent, and comparing the physiological response of the transgenic nonhuman animal having a transgene disrupting or interfering with $G\alpha_q$ to a control animal, wherein the same physiological response in the transgenic nonhuman animal as compared to the control animal indicates the specificity of the agent. In other words, the response in the normal or control animal and the response in the transgenic animal will indicate whether or not the agent has restored normal $G\alpha_q$ expression or activity. The physiological response of the test animal is compared to the physiological response of a control animal to determine the effect of the agent.

"Administering" the pharmaceutical composition of the present invention may be accomplished by any means known to the skilled artisan, such as, but not limited to, intravenous, intramuscular, intraperitoneal, and subcutaneous injection. A "control animal" is any animal of the same species which can be used as a reference standard. One specific, non-limiting example of a control animal is an untreated transgenic animal having a transgene disrupting or interfering with $G\alpha_q$. Another specific, nonlimiting example of a control animal is a nontransgenic animal of the same species, treated with the agent of interest. In yet another aspect, the control animal is the same nontransgenic animal having a transgene disrupting or interfering with $G\alpha_q$, wherein a control measurement is taken prior to administration of the agent, and a test measurement is taken at one or more time points after administration of the agent.

In another embodiment, a method is provided for determining an effect of an agent on $G\alpha_q$ expression.

In another embodiment, a method is provided for determining an adverse drug interaction with a $G\alpha_q$-inhibitor. An "adverse drug interaction" is an interaction or potentiation of an effect of an agent by inhibition of $G\alpha_q$, wherein interaction or potentiation of an effect of the agent by $G\alpha_q$ inhibition is not the intended utility of the agent. The method includes administering a test amount of an agent to a transgenic animal having a transgene disrupting or interfering with $G\alpha_q$, and measuring a physiological reaction of the animal. A "physiological response" is any biological or physical parameter of an animal which can be measured, as described above. The physiological response of the transgenic animal is then compared to the physiological response of a nontransgenic control animal of the same species administered the test amount of the agent. An "adverse physiological response" is an undesired change in a physiological parameter of the animal that is generally not considered beneficial to the animal. An specific, non-limiting example of an adverse physioloical response is hemorhage noted in an animal given an agent whose desired effect is a decrease in bleeding time.

If the agent of interest has the potential to interact adversely with a $G\alpha_q$-inhibitor, an adverse physiological response will be demonstrated in the transgenic animal having a transgene disrupting of interfering with $G\alpha_q$. Thus, an adverse response in the transgenic animal as compared to the control animal is indicative of an adverse drug interaction of the agent with $G\alpha_q$. A "test amount" is any amount of an agent which is suspected to interact with $G\alpha_q$ or to be potentiated by $G\alpha_q$ inhibition, either in vivo or in vitro. More than one dose of an agent of interest may be tested in the method of the invention in order to detect a physiological response.

Therapeutic Intervention

The present invention identifies the role of $G\alpha_q$ in platelet activation. As $G\alpha_q$ can be expressed in an altered manner as compared to expression in a normal cell it is possible to design appropriate therapeutic or diagnostic agents directed to this sequence. The polynucleotides encoding $G\alpha_q$ can be used to detect or to treat an $G\alpha_q$-associated disorder in a subject. A "subject" as used herein refers to any mammal, preferably a human. A "$G\alpha_q$-associated disorder" is any disorder associated with altered expression or function of $G\alpha_q$ in a subject (Gabbeta et al., *Proceedings of the National Academy of Sciences of the United States of America*, 94: 8750–8755 (1997). The term "ameliorate" denotes a lessening of the detrimental effect of a $G\alpha_q$-associated disorder in the subject receiving therapy. Essentially, any disorder which is etiologically linked to increased function or expression of $G\alpha_q$ could be considered susceptible to treatment with an agent which inhibits $G\alpha_q$, and any disorder which is etiologically linked to decreased function or expression of $G\alpha_q$ could be considered susceptible to treatment with an agent which augments $G\alpha_q$ expression or function.

The disorder typically is a disorder of platelets, wherein decreased function or expression of $G\alpha_q$ leads to a decrease in the ability of platelets activate. Several types of platelet disorders are known, including disorders of adhesion (e.g., Bernard-Soulier syndrome, von Willebrand's disease, and uremia), disorders of aggregation (e.g., Glanzmann's thrombasthenia, afibrinogenemia, dysproteinemias, and drug ingestion of ticlopidine, anti-IIb/IIIa antibodies), and disorders of granule release (e.g., Oculocutaneous albinism (Hemansky-Pudlak syndrome), Chediak-Higashi syndome, isolated dense granule deficiency, Gray-platelet syndrome, myoproliferative disorders, and drug-induced disorders from aspirin and other nonsteroidal anti-inflammatory agents (Handin, R. I., "Disorders of Platelets," In: *Harrison's Principles of Internal Medicine*, 14th Edition, Fauci et al. (eds.), McGraw-Hill, N.Y., pp. 636–743, 1998, herein incorporated by reference).

Alternatively, the disorder can be a disorder where an increase in the activity or expression of $G\alpha_q$ leads to an increase in the ability of platelets to activate. This disorder can be, but is not limited to, a disorder causing disseminated intravascular coagulation. One type of such a disorder is a disorder in the liberation of tissue factors, such as obstetrical syndromes (e.g., abruptio placentae, amniotic fluid embolism, a retained dead fetus, or a second trimester abortion), neoplasms (particularly mucinous adnocarcinomas and acute promyelocytic leukemia), intravascular hemolysis, fat embosim, and tissue damage (e.g., burns, frostbite, gunshot wounds). Another example of a disorder causing intravascular coagulation is endothelial damage such as that found in arctic aneurysm, hemolytic uremic syndrome, acute glomerulonephritis, or Rocky Mountain spotted fever. A third type of disorder associated with disseminated intravascular coagulation are infections such as bacterial infections (e.g., staphylococci, streptococci, pneumococci, meningococci, gram-negative bacilli, amongst others), viral infections (e.g., arboviruses, varicella, variolla, and rubella), parasitic infections (e.g., malaria, kala-azar), ricketssial infections (Rocky Mountain spotted fever), and mycotic infections (e.g., acute histoplasmosis) (Handlin, supra, 1998). Activation of platelets is also implicated in the pathogenesis of unstable angina, myocardial infarction, restenosis, embolus and stroke (Packham, M. A., *Can. J. Physiol Pharmacol* 72: 278–284, 1994; Coller, B. S., in: *The Heart and Cardiovascular System*, Fozzard, H. A., et al. (eds.) Raven, New York, pp. 219–273, 1992).

The term "agent" as used herein describes any molecule, e.g., protein, nucleic acid, or pharmaceutical, with the capability of altering the expression or function of $G\alpha_q$ Candidate agents include nucleic acids encoding $G\alpha_q$, or that interfere with expression of a $G\alpha_q$, such as an antisense nucleic acid, or a dominant negative variant of $G\alpha_q$, Candidate agents also encompass numerous chemical classes wherein the agent modulates $G\alpha_q$ expression or activity.

Treatment can include modulation of $G\alpha_q$ gene expression and $G\alpha_q$ activity by administration of a therapeutically effective amount of a reagent that modulates the $G\alpha_q$. The term "modulate" envisions the suppression of expression of $G\alpha_q$ when it is over-expressed, or augmentation of the expression of $G\alpha_q$ when it is under-expressed. Where a disorder is associated with the decreased expression of $G\alpha_q$, nucleic acid sequences that encode $G\alpha_q$ can be used. Where a disorder is associated with the increased expression of $G\alpha_q$, nucleic acid sequences that interfere with the expression of $G\alpha_q$ can be used. This approach utilizes, for example, antisense nucleic acid, ribozymes, or triplex agents to block transcription or translation of $G\alpha_q$ mRNA, either by masking that mRNA with an antisense nucleic acid or triplex agent, or by cleaving it with a ribozyme.

The present invention also provides gene therapy for the treatment of disorders which are associated with $G\alpha_q$ protein. Such therapy would achieve its therapeutic effect by introduction of a therapeutic polynucleotide into cells having the disorder. The "therapeutic polynucleotide" may be polynucleotide sequences encoding $G\alpha_q$, or antisense polynucleotide specific for $G\alpha_q$, designed to treat a $G\alpha_q$-associated disorder. Delivery of the therapeutic polynucleotide can be achieved using a recombinant expression vector such as a chimeric virus or a colloidal dispersion system. Especially preferred for therapeutic delivery of antisense sequences, or $G\alpha_q$ polynucleotides, is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV).

Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a $G\alpha_q$ sequence of interest into the viral vector, along with another gene which encodes the ligand for a receptor on a specific target cell, for example a receptor on a megakaryocyte, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the $G\alpha_q$ polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Q2, PA317, and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for the therapeutic polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley et al., *Trends Biochem. Sci.,* 6: 77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., *Biotechniques,* 6: 682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

The therapeutic agent can be targeted to a specific cell population, such as hematopoietic stem cells, progenitor cells, megakaryocytes, or platelets. Hematopoietic stem cells are rare cells that have been identified in fetal bone marrow, umbilical cord blood, adult bone marrow, and peripheral blood, which are capable of differentiating into each of the myeloerythroid (red blood cells, granulocytes, monocytes), megakaryocyte (platelets) and lymphoid (T-cells, B-cells, and natural killer cells) lineages. These cells are long-lived, and are capable of producing additional stem cells, a process termed self-renewal. Stem cells initially undergo commitment to lineage restricted progenitor cells, which can be assayed by their ability to form colonies in semisolid media. Progenitor cells are restricted in their ability to undergo multilineage differentiation and have lost their ability to self-renew. Progenitor cells eventually differentiate and mature into each of the functional elements of the blood. One such functional element is the megakaryocytes, which can produce platelets.

This invention involves administering to a subject a therapeutically effective dose of a pharmaceutical composition containing the agents of the present invention and a pharmaceutically acceptable carrier. "Administering" the pharmaceutical composition of the present invention may be accomplished by any means known to the skilled artisan.

The pharmaceutical compositions are preferably prepared and administered in dose units. Solid dose units are tablets, capsules and suppositories. For treatment of a patient, depending on activity of the agent, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, intravenously, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active agents, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, Science, 249: 1527–1533, 1990, which is incorporated herein by reference.

The pharmaceutical compositions according to the invention may be administered locally or systemically. By "therapeutically effective dose" is meant the quantity of an agent according to the invention necessary to prevent, to cure or at least partially arrest the symptoms of the disorder and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman And Gilman's: The Pharmacological Bases of Therapeutics,* 8th ed., Pergamon Press, 1990; and *Remington's Pharmaceutical Sciences,* 17th ed., Mack Publishing Co., Easton, Pa., 1990; each of which is herein incorporated by reference.

The following examples are intended to illustrate but not to limit the invention in any manner, shape, or form, either explicitly or implicitly. While they are typical of those that might be used, other procedures, methodologies, or techniques known to those skilled in the art may alternatively be used.

EXAMPLE 1

Generation of $G\alpha_q$ Mutant Mice

A genomic $G\alpha_q$ clone was isolated from a 129/Sv mouse genomic 1 phage library (Stratagene) with a probe derived from the $G\alpha_q$ cDNA. The genomic clone used for gene targeting contained the two last exons of the $G\alpha_q$ gene. To generate a null mutation, a 2.3-kb Bg/II fragment containing an exon coding for amino acids 246–297 of $G\alpha_q$ was replaced by the neo gene from plasmid pMCl neo PolyA (Stratagene). The targeting vector contained 5.5 kb of upstream sequence as the 5' arm and 2.6 kb of intron sequence as the 3' arm. Cells of the 129/Sv mouse embryonic stem cell line CJ7 were transfected with 20 µg linearized targeting vector by electroporation (Bio-Rad Gene Pulser set at 240 V and 500 µF). G418 selection (150 µg/ml geneticin; GIBCO/BRL) was added 24 h after transfection, and selected cell clones were isolated after 1 week of selection. Correctly targeted embryonic stem (ES) cell clones were identified by PCR using primers hybridizing to the neo cassette and to the intron sequence just outside the 3' arm of the targeting construct. Positive clones were confirmed by Southern blot analysis of ES cell DNA. DNA was digested with AflII and probed with a 1.3-kb DNA fragment from the 3' flanking region (FIG. 1A and B). Chimeric mice were generated using three independently targeted ES cell clones by aggregation of ES cells with CD1 morulae (Offermarns, S., et al., *Neurobiology* 94: 1408914094, 1997) or by injection of ES cells into C57/BL blastocysts (Bearer, E. L., *Cell Motil. Cytoskel.* 30: 50–66, 1995). Chimeras were bred with C57/BL and 129/Sv mice to generate hemizygous animals. The outbred mice (C57/BL) were more robust and showed higher fertility than the inbred (129/SV) mice. The outbred mice were used for most of the experiments. However, all of the results were repeated in the inbred animals, and no significant differences were found. Germ-line transmission was confirmed by PCR and Southern blot analysis.

Both wild-type and mutant mice utilized were of 129/Sv× C57BL/6 genetic background and were kept in the same room at the CIT transgenic animal facility.

EXAMPLE 2

Methods

Platelet Aggregation and Secretion

Whole blood was collected from mice during terminal bleeds while under pentobarbital anesthesia. Blood was collected from the inferior vena cava into heparinized syringes at a final concentration of 5U heparin/ml blood (Rosenblum, W. I., et al., Thromb. Res. 30: 347–355, 1983; Lad, N., et al. *Thromb. Res.* 46: 555–566, 1987). Whole blood from 8–11 $G\alpha_q$ (−/−) mice and wild-type littermates was collected and pooled for each platelet aggregation/ secretion study, and the studies were repeated three times. Optical platelet aggregation was performed using platelet rich plasma (PRP) which was prepared by centrifugation of whole blood at 350×g for 15 min. The PRP was aspirated, and the remaining blood was centrifuged at 2000×g for 15 min. to obtain platelet poor plasma (PPP). PPP was used as a reference to indicate 100% aggregation in the optical aggregation experiments. The PRP was adjusted to 500,000 platelets per µl using PPP as diluent. Optical aggregation experiments were conducted in a Chrono-Log platelet aggregometer. To determine aggregation response, 250 µl samples of PRP were added to the aggregometer chamber, where the light transmission is continually compared to PPP. Platelet ATP release was monitored by addition of firefly luciferase (7.3 µg/ml, final) and D-(−)-luciferin (800 units/ml, final) to all samples and by comparing the luminescence created by platelet ATP release to the luminesense generated by the addition of an ATP standard.

Bleeding Time

Bleeding times were determined in adult mice of 2–3 month age. Bleeding was initiated by amputation of 1 cm of the tail tip. The bleeding times were established while gently blotting emerging blood with a filter paper every 15 sec.

Thromboembolism Test

The mouse antithrombotic assay was basically performed as described (DiMinno and Silver, 1983, supra), as modified by Lawrence et al. (*J. Pharm. Sci* 83: 222–225, 1994). Mice were anesthetized with pentobarbital sodium (100 mg/kg), the jugular vein was exposed surgically, and a collagen/ epinephrine mixture (5 ml/kg of a saline based solution containing 150 µg/ml collagen and 100 µM epinephrine) was injected into the jugular vein at a controlled (about 20 µl/sec. Mice were observed for 1 h after injection.

EXAMPLE 3

Role of $G\alpha_q$ in Platelet Activation

To define the role of $G\alpha_q$ in platelet activation, platelets from $G\alpha_q$ deficient mice were examined (Offermanns, S., et al., Proc. Natl. Acad. Sci. 94: 14089–14094, 1997; Offermanns, S., et al., Nature 389: 183–186, both herein incorporated by reference) both in vitro and in vivo. Platelets from heterozygous animals show decreased levels of $G\alpha_q$ and in platelets from homozygous mutant mice no $G\alpha_q$ protein could be detected, while the levels of $G\alpha_{12}$, $G\alpha_{13}$ and $G\alpha_1$ were unaffected by the mutation. Most tissues express considerable levels of $G\alpha_{11}$, however, no $G\alpha_{11}$ was present in platelets from wild-type or $G\alpha_q$ deficient mice. As shown in FIG. 1 and Table 1, platelets isolated from wild-type mice aggregated and released ATP in response to collagen, arachidonic acid, thrombin, and the $TXA_2$ receptor agonist U46619.

TABLE 1

Platelet aggregation and ATP release in wild-type and $G\alpha_q$ deficient platelets

|  | Aggregation (%) | | ATP release (nmoles) | |
| --- | --- | --- | --- | --- |
|  | wild-type | $G\alpha_q(-/-)$ | wild-type | $G\alpha_q(-/-)$ |
| ADP (10 μM) | 61.3 ± 19.4 | 3.7 ± 6.5 | 0.0.6 ± 0.06 | 0.12 ± 0.21 |
| Collagen (10 μg/ml) | 77.1 ± 12.6 | 2.0 ± 1.7 | 1.35 ± 0.63 | 0.07 ± 0.12 |
| Arachidonic acid (0.5 mM) | 66.9 ± 0.8 | 0.0 ± 0.0 | 0.52 ± 0.03 | 0.0 ± 0.0 |
| U-46619 (10 μg/ml) | 77.1 ± 6.9 | 0.0 ± 0.0 | 0.72 ± 0.12 | 0.0 ± 0.0 |
| Thrombin (1 U/ml) | 28.8 ± 8.8 | 0.0 ± 0.0 | 0.36 ± 0.30 | 0.0 ± 0.0 |
| A23187 (100 μM) | 77.6 ± 1.8 | 69.2 ± 10.8 | 4.79 ± 1.05 | 3.08 ± 2.00 |
| PMA (100 μM) | 70.7 ± 6.2 | 77.5 ± 8.9 | 0.24 ± 0.04 | 0.13 ± 0.18 |

Table 1 Platelets were incubated with the indicated concentrations of agents. Shown are mean values of triplicates ±S.D.

ADP induced aggregation of wild-type platelets but did not lead to significant ATP release. In contrast, $G\alpha_q$ deficient platelets failed to aggregate or to release ATP contents following the addition of any of the activators. To test whether $G\alpha_q$ deficient platelets were able to aggregate and to release their granule contents, the effects of the calcium ionophore A23187 were examined. A23187 led to dramatic secretion and aggregation in both wild-type and $G\alpha_q$ deficient platelets. Similarly, the phorbol ester phorbol 12-myristate 13-acetate (PMA) was able to induce platelet aggregation in both $G\alpha_q$ deficient and wild-type platelets, presumably by protein kinase C mediated activation of the fibrinogen receptor glycoprotein IIb/IIIa (integrin $\alpha_{IIb}\beta_3$) (Shattil, S. J., et al., Curr. Opin. Cell Biol. 6: 695–704, 1994). Thus, $G\alpha_q$ deficient platelets contain granules and functional fibrinogen receptors, and the release and aggregation mechanisms are intact and can be activated by stimulation of downstream targets. Interestingly, platelets of $G\alpha_q$ (-/-) mice when exposed to a variety of activators were still able to undergo shape change, which is apparently due to a fast reorganization of actin filaments (Bearer, 1995, supra). This suggests that different G-proteins, e.g., $G_1$, $G_{12}$ or $G_{13}$, are involved in the induction of platelet shape change.

It was occasionally observed that newborn $G\alpha_q$ (-/-) pups suffered from overt intra-abdominal bleeding which in most cases resulted in postnatal death. A similar phenotype has been reported in fibrinogen deficient mice, and is probably due to minor traumata during the birth process or during adaptation to extrauterine life (Suh, T. T., et al., Genes Dev. 9: 2020–2033, 1995). Blood platelet counts were not significantly different in wild-type and $G\alpha_q$ deficient mice (678±153×10³/μl in wild-type [n=4] vs. 603±162×10³/μl in $G\alpha_q$ (-/-) animals [n=5]. To test whether the unresponsiveness of $G\alpha_q$ deficient platelets in vitro correlated with a bleeding diathesis in the $G\alpha_q$ (-/-) mice, the bleeding times were determined, which are an in vivo measure of platelet dependent primary hemostasis. While wild-type and heterozygous (data not shown) mice were able to control bleeding induced by the amputation of the tail tip within 4–8 min, $G\alpha_q$ deficient mice continued to bleed for the length of the observation period (up to 30 min.) (FIG. 2A), indicating that the loss of $G\alpha_q$ resulted in defective primary hemostasis. Intravascular platelet aggregation and thrombosis participate in a variety of pathological processes as well as in thrombotic complications resulting from acute clinical procedures like thrombolysis and angioplasty (Packham, M. A., Can. J. Physiol. Pharmacol. 72: 278–284, 1994; Coller, B. S., in The Heart and Cardiovascular System, pg. 219–273, Fozzard, H. A. et al. eds., Raven Press, New York, 1992; McMurray, J., and Rankin, A., Br. Med. J. 309: 1343–1350, 1994).

To examine whether $G\alpha_q$ (-/-) mice are protected against platelet dependent thromboembolism, the "mouse antithrombotic assay" was employed (DiMinno, G., and Silver, M. J., J. Pharmacol. Exp. Ther. 225: 57–60, 1983). When wild-type mice were given an intravenous injection of a mixture of collagen and epinephrine, all animals died within 5 min due to platelet thromboembolism in the microcirculation of the lungs (DiMinno and Silver, 1983, supra) (FIG. 2B). In contrast, $G\alpha_q$ deficient mice survived the challenge for a 1 hr observation period. Thus, $G\alpha_q$ (-/-) mice are resistant to thromboembolism induced by platelet activation in vivo.

The in vivo observations correlate well with the results of in vitro platelet aggregation studies in $G\alpha_q$ (-/-mice. They clearly delineate the involvement of $G\alpha_q$ in the transduction of physiological and clinically relevant signals in platelets. The $G\alpha_q$ mediated stimulation of PLC-β isoforms appears to be the central pathway through which various platelet activators induce granule release and activation of the fibrinogen receptor (FIG. 2C). $G\beta_\gamma$subunits released from activated $G_1$ may contribute to the receptor dependent activation of PLC-β, however, this mechanism is apparently not able to compensate the lack of $G\alpha_q$. Besides its role in the inhibition of adenylyl cyclase, $G_1$ and/or $G_{12/13}$ seem to be involved in the induction of shape change. Thus, each of the different G-protein mediated circuits appear to affect different stages of platelet function. In addition, the data suggest that $G\alpha_q$ represents a new target for the development of antiplatelet agents. $G\alpha_q$ deficient mice have recently been described to suffer from ataxia as a result of the absence of $G\alpha_q$ in the cerebellar cortex (Offermanns, et al., 1997, supra). However, the presence of the blood-brain barrier might allow for an antiplatelet effect without neurologic side effects.

Although the invention has been described with reference to the presently preferred embodiments, it should be understood that various modifications can be made without departing from the spirit of the invention. Accordingly, the invention is limited only by the following claims.

What is claimed is:

1. A transgenic mouse whose genome comprises a homozygous disruption of the endogenous $G\alpha_q$ gene, wherein said disruption comprises the insertion of a transgene comprising a selectable marker sequence, and wherein said disruption results in said mouse lacking detectable levels of $G\alpha_q$ such that a platelet derived from said transgenic mouse is unresponsive to a platelet activator as compared to a platelet derived from a nontransgenic mouse of the same species.

2. The transgenic mouse of claim 1, wherein said insertion results from homologous recombination.

3. An in vitro cell, wherein said cell is derived from the transgenic mouse of claim 1, and wherein said cell comprises a genome comprising a homozygous disruption of the endogenous $G\alpha_q$ gene, wherein said disruption comprises the insertion of a transgene comprising a selectable marker sequence.

4. A cell line derived from the transgenic animal of claim 1, wherein said cell line comprises a genome comprising a homozygous disruption of the endogenous $G\alpha_q$ gene, wherein said disruption comprises the insertion of a transgene comprising a selectable marker sequence.

5. A method for producing a transgenic mouse homozygous for a disruption in a $G\alpha_q$ gene, comprising:

a) introducing a transgene in operable linkage with at least one expression regulatory sequence into an embryo of a mouse such that insertion of said transgene results in the disruption of one allele of the murine endogenous $G\alpha_q$ gene and comprises the insertion of a transgene comprising a selectable marker sequence;

b) transplanting the embryo of a) into a pseudopregnant mouse;

c) allowing said embryo to develop to term such that said pseudopregnant mouse gives birth to a chimeric mouse comprising a disrupted $G\alpha_q$ gene in its germ line;

d) breeding said chimeric mouse to produce a heterozygous mouse comprising a disrupted $G\alpha_q$ gene;

e) mating together a male and female mouse each heterozygous for said disrupted $G\alpha_q$ gene and identifying progeny that are homozygous for said disrupted $G\alpha_q$ gene, wherein loss of expression of $G\alpha_q$ results in a platelet derived from said progeny homozygous for said disrupted $G\alpha_q$ gene being unresponsive to a platelet activator as compared to a platelet derived from a nontransgenic mouse of the same species.

6. The method of claim 5, wherein the introduction of the transgene into the embryo is by introducing an embryonic stem cell into the embryo, wherein said embryonic stem cell comprises a genome comprising a hemizygous disruption of the endogenous gene, wherein said disruption comprises the insertion of a transgene comprising a selectable marker sequence.

7. The method of claim 5, wherein the introduction of the transgene into the embryo is by infecting the embryo with a virus containing the transgene.

8. The method of claim 7, wherein the virus is a retrovirus.

9. An isolated polynucleotide encoding the two last exons of the $G\alpha_q$ gene and having a region containing an exon coding for amino acids 246–297 of $G\alpha_q$ replaced by a heterologous nucleic acid sequence.

10. The polynucleotide of claim 9, wherein the heterologous nucleic acid sequence is a neo gene.

* * * * *

UNITED STATES PATENT AND TRADEMARK OFFICE
CERTIFICATE OF CORRECTION

PATENT NO. : 6,028,244
DATED : FEBRUARY 22, 2000
INVENTOR(S) : CHRISTOPHER F. TOOMBS AND STEFAN OFFERMANNS

It is certified that error appears in the above-identified patent and that said Letters Patent is hereby corrected as shown below:

On the Title Page

Please amend the assignee in the above-referenced patent to include:

AMGEN, INC., Thousand Oaks, California

Therefore, the assignee should be read as follows:

California Institute of Technology, Pasadena, California
    AMGEN, Inc., Thousand Oaks, California Signed and Sealed this Seventeenth Day of April, 2001

*Attest:*

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO. : 6,028,244
DATED : February 22, 2000
INVENTOR(S) : Christopher F. Toombs, Stephen Offermanns and It is certified that error appears in the above-identified patent and that said Letters Patent is hereby corrected as shown below:

Column 1,
Before FIELD OF INVENTION, please insert the following:
"STATEMENT AS TO FEDERALLY-SPONSORED RESEARCH
The U. S. Government has certain rights in this invention pursuant to Grant No. GM 342236 awarded by National Institute of Health."

Signed and Sealed this

Eighteenth Day of September, 2001

Attest:

*Nicholas P. Godici*

NICHOLAS P. GODICI
*Attesting Officer*     *Acting Director of the United States Patent and Trademark Office*